United States Patent [19]

Euzen et al.

[11] 4,210,015
[45] Jul. 1, 1980

[54] DEVICE FOR FOLLOWING THE VARIATIONS IN THE COMPOSITION OF A FLOWING HETEROGENEOUS LIQUID MIXTURE

[75] Inventors: Jean-Paul Euzen, Ecully; Patrick Scemama, Paris, both of France

[73] Assignees: Institut Francais du Petrole, Rueil-Malmaison; Societe Anonyme Pipe Line Service, Puteaux, both of France

[21] Appl. No.: 970,306

[22] Filed: Dec. 18, 1978

[30] Foreign Application Priority Data

Dec. 19, 1977 [FR] France .................. 77 38561

[51] Int. Cl.² ........................................... G01N 11/00
[52] U.S. Cl. ................................................. 73/61.1 R
[58] Field of Search .................... 73/61.1 R, 61 R, 53, 73/195, 196

[56] References Cited

U.S. PATENT DOCUMENTS

| 3,638,476 | 2/1972 | Paterson et al. | 73/61.1 R |
| 3,924,449 | 12/1975 | Moreau et al. | 73/61.1 R |
| 4,055,986 | 11/1977 | Stewart et al. | 73/61.1 R X |

FOREIGN PATENT DOCUMENTS 1171795  11/1969  United Kingdom ................. 73/61.1 R

*Primary Examiner*—Gerald Goldberg
*Assistant Examiner*—Joseph W. Roskos
*Attorney, Agent, or Firm*—Millen & White

[57] ABSTRACT

The device repeatedly samples a selected amount of liquid mixture and separates at least one liquid phase from the mixture. The amount of the separated liquid phase is plotted versus the corresponding amount of the sampled mixture. At least some of the sample is recycled.

13 Claims, 4 Drawing Figures

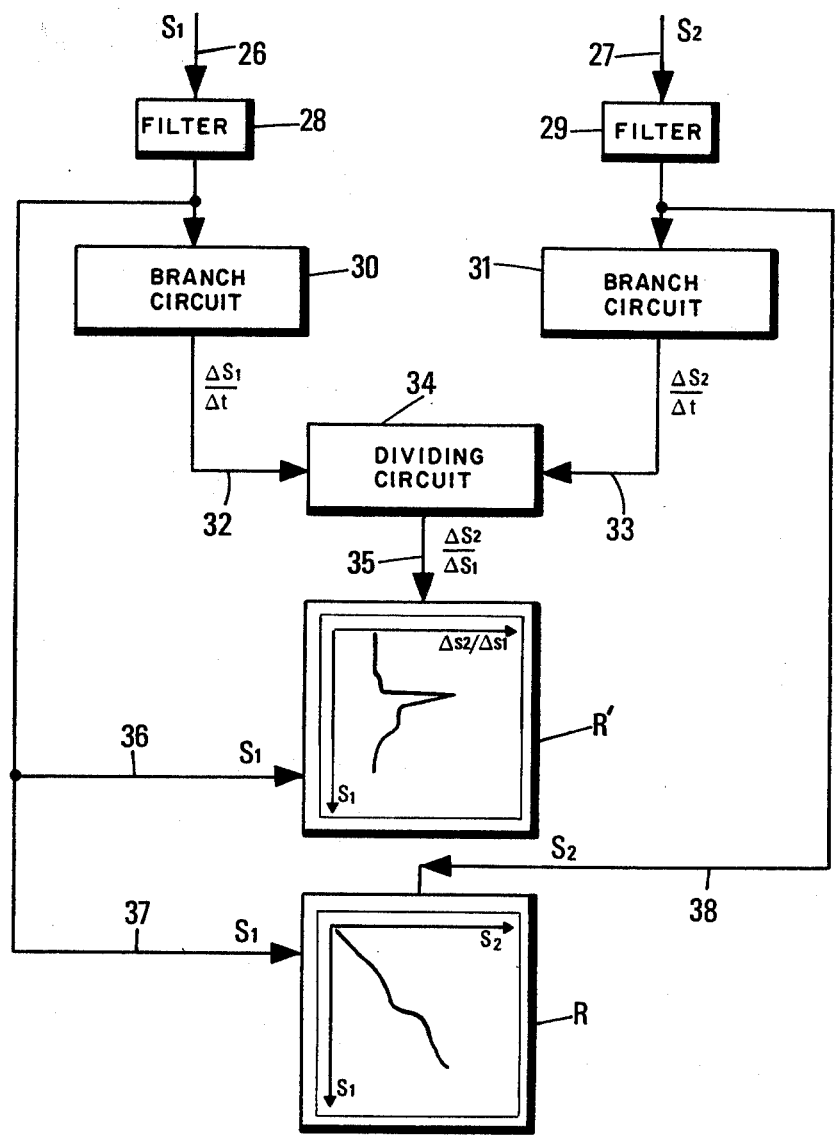

DEVICE FOR FOLLOWING THE VARIATIONS IN THE COMPOSITION OF A FLOWING HETEROGENEOUS LIQUID MIXTURE

BACKGROUND OF THE INVENTION

When conveying heterogeneous mixtures essentially containing different barely miscible liquid phases, it is often important to know with accuracy the percentage of each phase in the mixture. Moreover when such mixtures flow through pipes at a high rate, it is often of interest to follow in a continuous manner the variation of these contents versus time.

Thus, for example, when loading and unloading a tanker ship, a storage tank, etc., it is important to know the insoluble water content of the crude oil, or of the flowing valuable product.

At the present time, there does not exist any apparatus enabling such measurement in a precise and reliable manner. For example, regarding the "water+sediment" content of a crude oil, a conventional standard recommends collecting a single 100 cc sample for an entire shipload and analyzing this sample by centrifugation.

This yields only an extremely inaccurate, or even uncertain picture of the actual composition of the whole shipload, since due to the specific gravity differences of the phases, such a shipload is far from being homogeneous. In particular, it is possible to collect samples containing nearly no water when drawing off the upper layers of a product which is lighter than water, or, conversely, to collect only water when withdrawing the lower layer.

Apparatuses already exist for measuring the composition of a flowing medium, but such apparatuses either do not permit determination of the free water content of the medium (as is the case with apparatuses measuring electric conductivity), or do not provide for a precise and continuous determination (in the case of distillation apparatuses).

Microsensors determining an effective permittivity of the heterogeneous mixture can hardly be used when the mixture is a crude oil due to its viscosity. Moreover, a water or oil drop clogging the microsensor may affect all the measurements.

SUMMARY OF THE INVENTION

To obviate these disadvantages, a sampling-analyzing device has been designed, according to this invention, whereby samples can be collected as a function of time or of the flow rate of the product to be analyzed, and which enables separation and analysis of the collected samples to be carried out by continuous centrifugation.

With this reliable and accurate device, the percentages of insoluble liquid and solid in the mixture to be analyzed can be determined either as a function of time, or in relation to the discharge flow rate.

The device according to the invention comprises:
(a) means for sampling an adjustable selected amount of the flowing mixture,
(b) means connected to said sampling means, for separating at least one liquid phase from the mixture,
(c) means for measuring the amount of the so-separated liquid phase, and,
(d) means for displaying the measured value of this amount and the value of the amount of sampled mixture, said displaying means being connected both to said sampling means and to said measuring means.

This device is characterized by the combination of sampling means of variable flow rate, continuous separation means, and means for recycling at least one liquid phase issuing from said separating means, said recycling means being connected to said separating means and to the flow of heterogeneous mixture downstream of the point where said sampling means is connected to this flow.

BRIEF DESCRIPTION OF THE DRAWINGS

The invention is illustrated by the accompanying drawings, wherein

FIG. 4 illustrates another embodiment of the device according to the invention.

DETAILED DESCRIPTION

Figure 1:
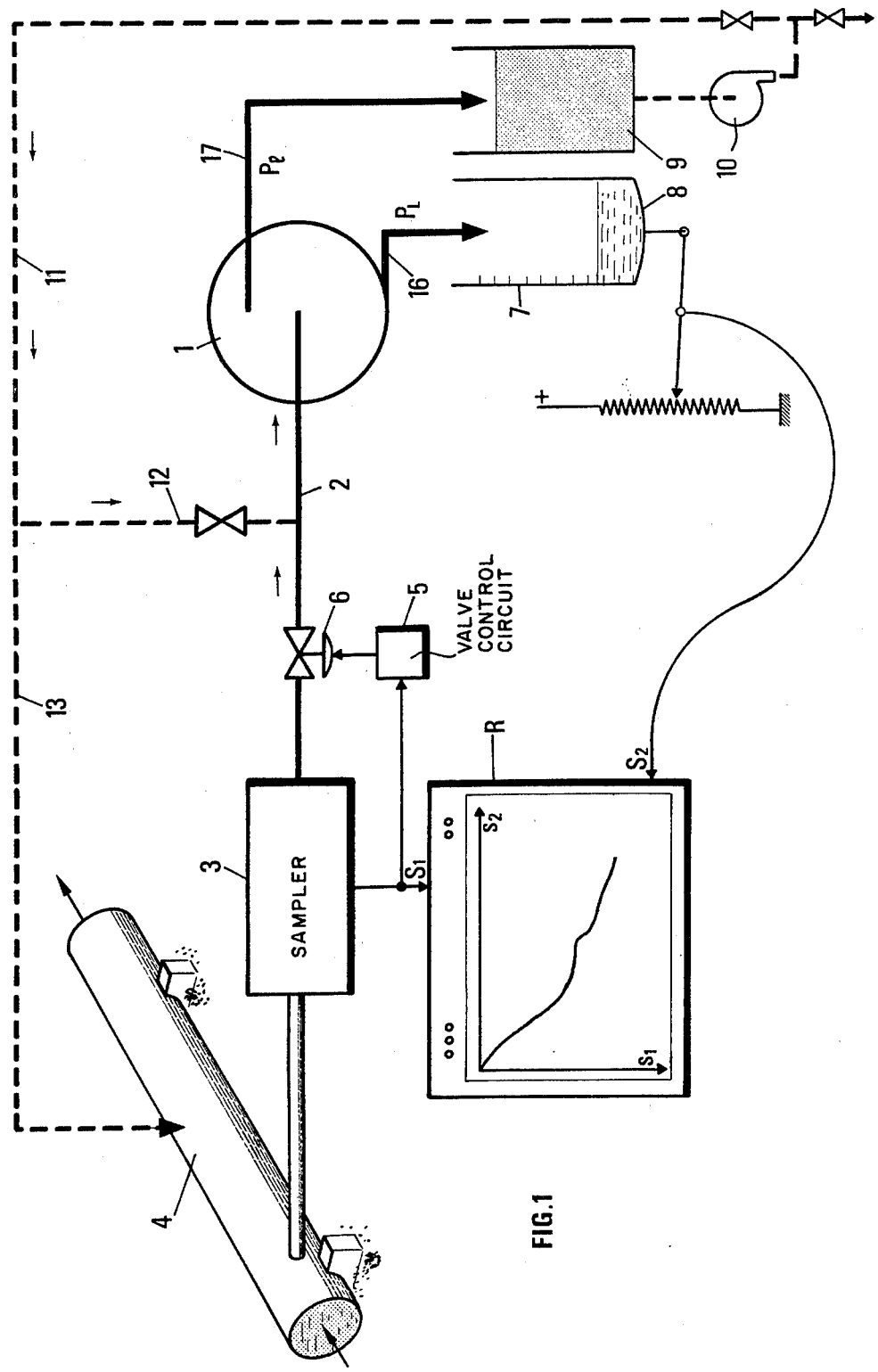
FIG. 1 diagrammatically shows a device according to the invention.

In the diagram of FIG. 1, the device is formed by the combination of several elements comprising a centrifugal machine 1 providing continuous separation of a heavy phase, such as for example "water+sediments" and another insoluble light phase of lower specific gravity, such as for example crude oil.

This centrifugal machine is fed through a pipe 2, connected to an automatic sampler 3 which collects samples, for example, from a pipe 4 permanently scavenged by the main flow (whose direction of flow is indicated by arrows), or by a fraction of this main flow. The volume of each sample collected by sampler 3 is fixed during the whole sampling period, but can be changed according to need, for example, from 1 cc to 1,000 cc, but preferably from 10 cc to 300 cc.

The samples may be collected either at constant time intervals, e.g. at least one sample every second without any upper limit, or at time intervals varying as a function of the main flow rate which is separately measured. This second possibility enables a sample to be systematically collected as soon as a preselected volume has passed by a given point.

Every time a preselected amount of the flowing mixture has been collected, sampler 3 delivers a pulse to a first terminal of a recording device R, which causes for example unreeling of a certain length of the recording paper of the device R. The unreeled paper length is thus proportional to the sampled mixture amount. This signal $S_1$ also energizes a circuit 5 opening an electrovalve 6 which permits passage of the volume collected by the sampler 3 into pipe 2 connected to the centrifugal machine 1.

More generally the device R may consist of any means for displaying or/and recording the amount of mixture collected.

Before its introduction into centrifugal machine 1, the outflow of the sampler is joined with an additional flow, in a manner to be indicated hereinafter.

These two flows feed into the centrifugal machine 1 which separates the insoluble phases by the effect of centrifugation with a high acceleration.

In the analysis of water-containing crude oil, the water heavy phase $P_L$, flows to the periphery of the chamber rotating at high speed while the light phase $P_l$ formed of crude oil remains in the central portion of this chamber. It is then possible to collect the heavy phase separately in container 7.

This container comprises, for example, at its bottom a membrane 8 which is connected via a system of hinged rods to the slider of a potentiometer, measuring by a signal $S_2$ the pressure applied to the membrane 8, this pressure being proportional to the collected amount of water. Signal $S_2$ is transmitted to the recorder which thereby records this amount in relation to the overall amount of mixture which has flown through the sampler, this last amount being represented by signal $S_1$. There can be derived therefrom at any time, for example at the end of the discharge phase, the average percentage of the heavy phase in the mixture.

By following the variation of the slope $\Delta S_2/\Delta S_1$ of the curve representing the amount of heavy phase versus the amount of sampled crude oil, the evolution of the percentage of heavy phase in the mixture can also be determined.

In one embodiment, the signal $S_2$ is introduced into a shunting electronic circuit producing a signal $S_3$, proportional to the ratio $\Delta S_2/\Delta S_1$.

This signal $S_3$ may be recorded versus time either continuously or intermittently. The signal $S_3$ may optionally be used for actuating an alarm when the value of the ratio $\Delta S_2/\Delta S_1$ becomes greater than a selected limit-value.

FIG. 4 illustrates another embodiment whereby there can be recorded not only the signal $S_2$ (representative of the water content) as a function of the signal $S_1$ (overall mixture amount), but also the variations of the ratio $\Delta S_2/\Delta S_1$, as a function of the amount of sampled crude oil.

Electrical conductors 26 and 27, which are respectively connected to the sampler 3, delivering signal $S_1$, and to the potentiometer delivering signal $S_2$, are connected to shunting circuits through filters (filters 28 and 29, branch circuits 30 and 31). The shunts 30 and 31 are in turn connected to a dividing circuit 34 through conductors 32 and 33 respectively. The dividing circuit 34 delivers a signal proportional to the ratio $\Delta S_2/\Delta S_1$, this signal feeding through conductor 35 into a first input terminal of a displaying or recording device R'. This device receives signal $S_1$ on a second input terminal connected through conductor 36 to the output terminal of filter 28.

A displaying or recording device R similar to that of FIG. 1 which receives signals $S_1$ and $S_2$, is connected to the output terminal of filters 28 and 29 through conductors 37 and 38 respectively.

The dividing circuit 34 may be connected to a (not shown) warning circuit delivering a sound or/and light signal when the value of the ratio $\Delta S_2/\Delta S_1$ exceeds a selected limit-value.

It will also be possible to use a warning device which directly detects practically pure water flowing through pipe 2, or through the sampling pipe connecting sampler 3 to pipe 4.

The light phase, which consists of crude oil in the example of a crude oil-water mixture, flows out of the centrifugal machine and after a temporary storage at 9 is recycled under pressure by pump 10, both to the inlet of centrifugal machine 1, through pipes 11 and 12, and through pipe 13, to a point of pipe 4 downstream of the location where sampling is effected.

Such partial recycling of the light phase through pipes 11 and 12 has the advantage of attenuating the flow rate fluctuations resulting from the discontinuous sampling effected by sampler 3.

Moreover such arrangement enhances the quality of the separation and has the additional advantage of attenuating the variations in the residence time of the mixture in centrifugal machine 1.

While the above description relates, for illustration purposes, to the particular example of the determination of the water content of a crude oil, the described apparatus could be used as well for recording the content of the light phase, such as for example the oil content of a water-in-oil emulsion. For this purpose, it would be sufficient to collect the light phase in container 7 and conversely to transfer the heavy phase into the temporary storage tank 9.

More generally, according to particular requirements, either of the two liquid phases will be recycled as hereinabove described.

Whenever there is a dispersed solid phase in addition to the liquid phases in the heterogeneous mixture to be analysed, it is also possible to provide for such a solid phase.

This solid phase will generally have in its compact form a higher density than the heavy phase $P_L$ and will thus be spread on the wall of the bowl of centrifugal machine 1. Depending on the amount of solid phase, it will be possible to discharge this solid phase periodically during operation, without stopping the rotation of centrifugal machine 1 utilizing suitable known means. If however, the solid phase content is small compared to the size of the bowl of the centrifugal machine 1, it will be possible to collect the whole amount of this solid phase at the end of the operation.

Figure 2:
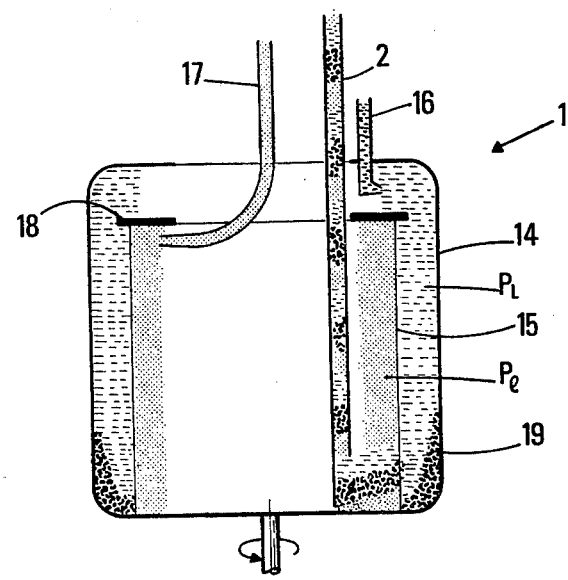
FIG. 2 diagrammatically illustrates the centrifugal machine.

FIG. 2 diagrammatically shows the bowl 14 of a centrifugal machine of a known type which may be used in the device according to the invention. This bowl which is rotated at a high speed is fed with heterogeneous liquid mixture from pipe 2. Under this influence of the centrifugal force, the two liquid phases $P_L$ and $P_l$ of different specific gravities are separated, thus forming an interface 15.

The liquid phases can be discharged, through pipes 16 and 17 respectively, these pipes collecting the two liquids on either sides of a diaphragm 18.

The solid which may be present in the mixture is gathered against the internal wall of bowl 14 in an annular zone 19 wherefrom it can be discharged at the end of the operation.

As indicated above, bowl 14 may be provided with means for continuously discharging this solid.

Figure 3:
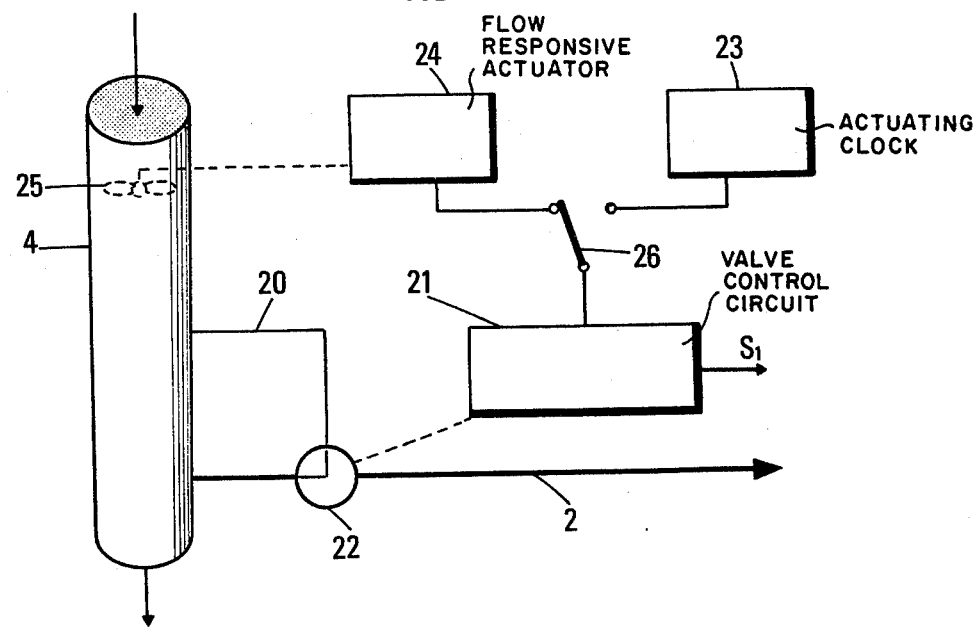
FIG. 3 diagrammatically shows an embodiment of a sampling device.

The sampling system which is shown by way of example in FIG. 3 comprises a pipe 20 for deriving a fraction of the main flow from pipe 4. An electronic circuit 21 makes it possible, by actuating one or several electro-valves 22, to direct the fluid flowing through pipe 20 either back to the main pipe 4, or to pipe 2 connected to centrifugal machine 1. This circuit 21 which delivers electric control pulses is either periodically actuated by a clock 23, or controlled by a device 24 which receives from a flowmeter 25 an indication as to the fluid flow rate, through pipe 4 (upstream of the connection point 20, in the illustrated embodiment).

A switch 26 makes it possible to select one of the two above-indicated operating modes for actuating the control device 21.

Signals $S_1$ are delivered by the circuit 21 to the first input terminal of a recording device R (FIG. 1), as indicated above.

Improvements or modifications can be made without departing from the scope of the present invention.

For example, shunting pipe 20 may send the liquid mixture through a microsensor having a mouthpiece located in pipe 4 at an adjustable distance from the pipe axis.

It will thus be possible to collect a sample which is really representative of the fluid flow in pipe 4, taking into account the velocity distribution in a cross-section of this pipe.

It will moveover be possible to use a sampler 3 of a type permitting substantially continuous sampling from pipe 4, at a flow rate depending on the flow rate in this pipe, this sampler comprising for example a metering pump whose flow rate is controlled by the flow rate of the liquid medium in pipe 4.

We claim:

1. A device for following the variations in the composition of a flowing heterogeneous mixture of at least two liquid phases incompletely miscible with each other, the device comprising:
    (a) means for sampling an adjustably selected amount of the flowing mixture to provide a sample thereof,
    (b) means for measuring the amount of said sample,
    (c) means connected to said sampling means, for separating at least one liquid phase from said sample of the mixture,
    (d) means for measuring the amount of the so-separated liquid phase,
    (e) means for displaying the measured values of the amounts of said sample of mixture and of said separated liquid phase, said displaying means being connected to both of said amount measuring means, and, means for recycling at least one liquid phase issuing from said separating means, said recycling means being connected to said separating means and to the flow of heterogeneous mixture downstream of the point where said sampling means is connected to said flow.

2. A device according to claim 1, wherein said separating means comprises continuous centrifuging means.

3. A device according to any of claims 1 or 2, wherein said sampling means is directly connected to the flow of said heterogeneous mixture.

4. A device according to any of claims 1 and 2, wherein said sampling means is connected to a derivation of the flow of heterogeneous mixture.

5. A device according to claim 1, comprising a sensor positionable in the flowing mixture at an adjustable distance from the flow axis.

6. A device according to claim 1, wherein said sampling means is an intermittently operating device adapted to effect sampling according to a preselected time schedule.

7. A device according to claim 1, wherein said sampling means is an intermittently operating device provided with means for controlling the sampling frequency as a function of the flow rate of heterogeneous mixture.

8. A device according to claim 1, wherein said sampling means is continuously operating and is provided with means for controlling the sampled flow rate as a function of the flow rate of the heterogeneous mixture.

9. A device according to claim 1, further comprising additional means for calculating a ratio $\Delta S_2/\Delta S_1$, wherein $\Delta S_2$ is the variation of said measured amount of separated liquid phase corresponding to a slight variation $\Delta S_1$ in said measured amount of sampled mixture.

10. A device according to claim 9, further comprising alarm means adapted to be actuated when the ratio $\Delta S_2/\Delta S_1$ exceeds a preselected limit-value.

11. A device according to claim 1, which can be used for heterogeneous mixtures also containing a solid phase, wherein said separating means is of a type permitting discharge of the solid phase without interrupting the operation of said separating means.

12. The device of claim 1, wherein said sampling means is of variable sampling rate.

13. The device of claim 1, wherein said separation means is a continuous separating means.

* * * * *